(12) United States Patent
Lee et al.

(10) Patent No.: US 10,100,065 B2
(45) Date of Patent: Oct. 16, 2018

(54) COMPOUND FOR LABELING MITOCHONDRIA AND METHOD OF PRODUCING THE SAME

(71) Applicant: KOREA INSTITUTE OF SCIENCE AND TECHNOLOGY, Seoul (KR)

(72) Inventors: Jun-Seok Lee, Seoul (KR); Dhiraj P. Murale, Seoul (KR); Seong-Cheol Hong, Seoul (KR); Seok Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 86 days.

(21) Appl. No.: 15/479,150

(22) Filed: Apr. 4, 2017

(65) Prior Publication Data

US 2017/0327518 A1    Nov. 16, 2017

(30) Foreign Application Priority Data

May 11, 2016 (KR) .......................... 10-2016-0057717

(51) Int. Cl.
| | |
|---|---|
| *C07F 5/02* | (2006.01) |
| *C09B 69/00* | (2006.01) |
| *C07F 9/6561* | (2006.01) |
| *C09K 11/06* | (2006.01) |
| *G01N 33/58* | (2006.01) |

(52) U.S. Cl.
CPC ............ *C07F 5/027* (2013.01); *C07F 9/6561* (2013.01); *C09B 69/001* (2013.01); *C09K 11/06* (2013.01); *G01N 33/582* (2013.01); *C09K 2211/1433* (2013.01); *C09K 2211/1466* (2013.01)

(58) Field of Classification Search
CPC ................................ C07F 5/027; C09B 69/001
See application file for complete search history.

(56) References Cited

FOREIGN PATENT DOCUMENTS

| JP | 08-6245 | * 1/1996 | ............. G03F 7/029 |
|---|---|---|---|
| KR | 10-2009-0119283 A | 11/2009 | |

* cited by examiner

Primary Examiner — Joseph R Kosack
(74) Attorney, Agent, or Firm — Goldilocks Zone IP Law

(57) ABSTRACT

This invention relates to a compound for labeling mitochondria and a method of producing the same, wherein the compound is represented by Chemical Formula 1 or Chemical Formula 2 below, and is useful in labeling mitochondria.

[Chemical Formula 1]

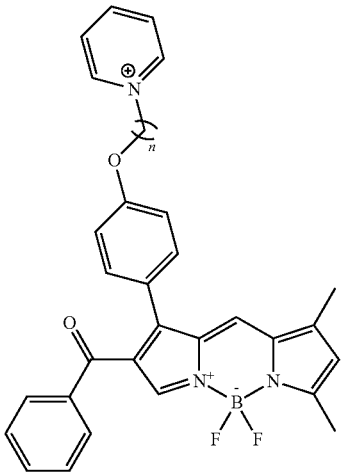

[Chemical Formula 2]

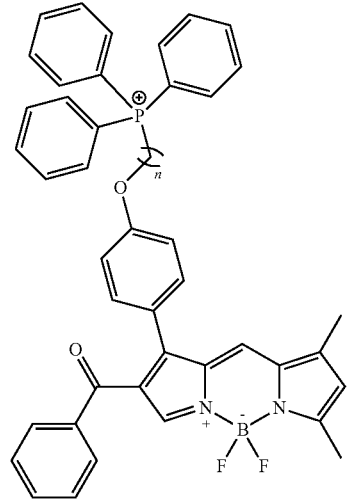

In Chemical Formulas 1 and 2, n is 4 or 10.

7 Claims, 1 Drawing Sheet
(1 of 1 Drawing Sheet(s) Filed in Color)

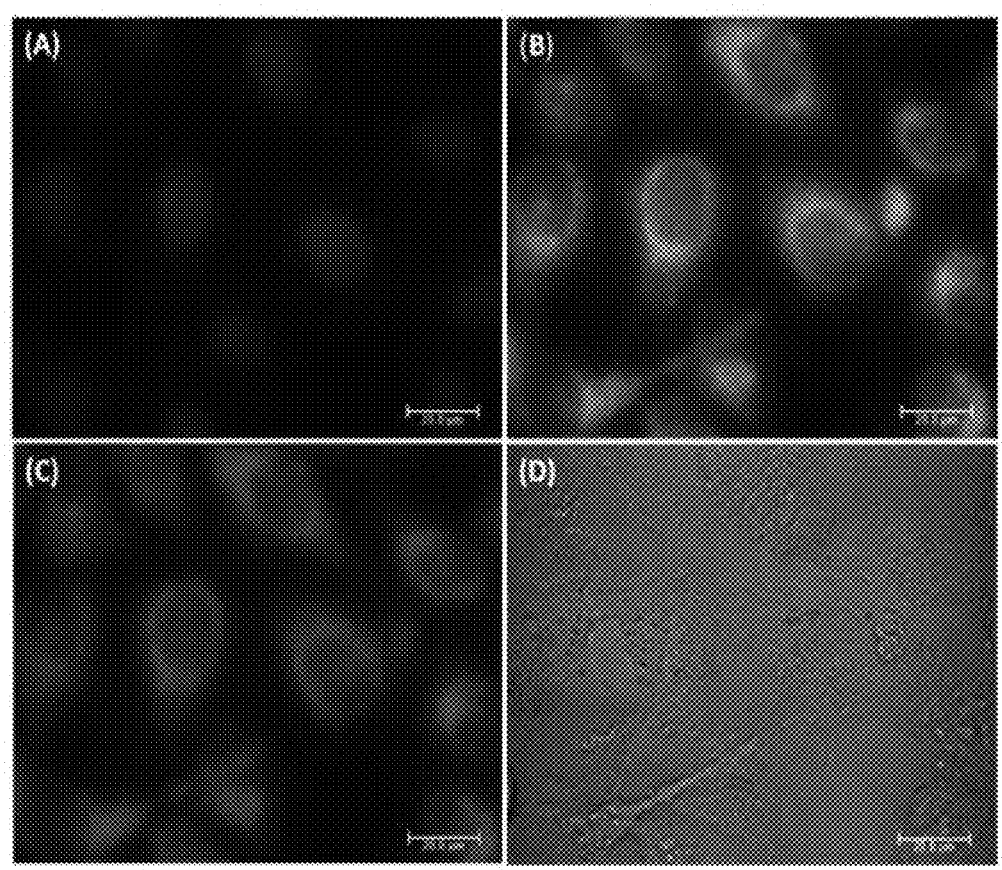

COMPOUND FOR LABELING MITOCHONDRIA AND METHOD OF PRODUCING THE SAME

CROSS REFERENCE TO RELATED APPLICATION

The present application claims the benefit of Korean Patent Application No. 10-2016-0057717 filed on May 11, 2016.

BACKGROUND OF THE INVENTION

1. Field of the Invention

The present invention relates to a compound for labeling mitochondria and a method of producing the same.

2. Description of the Related Art

With the advancement of OMICS technology, thorough research is ongoing into understanding the control of protein expression at the subcellular level. In particular, proteomics based on cell organelles has the potential to be useful in the diagnosis and treatment of disease by revealing and controlling the mechanism of protein residing in target organelles and an increase or decrease in intracellular concentration thereof due to stimulation. Furthermore, mitochondria are one of the subcellular organelles essentially associated with cancer development, such as energy metabolism, biosynthesis, and signal transmission, and are being studied from various points of view for anticancer treatment, etc. Here, such studies are carried out through the spread of a high-resolution fluorescence microscope, whereby the resolution limit of existing optical microscopes may be overcome, and observing organelles and identifying new mechanisms become possible. Commonly useful methods for labeling the intracellular organelles and specific proteins (toxic substances) are a transfection process involving a green fluorescence protein (GFP) using a virus, as disclosed in the following Patent Document.

However, the conventional method is problematic in terms of gene mutation because the resolution is limited due to the large size of about 27 kDa and because the virus is characterized in that its traits are randomly injected into the DNA of the infectious agent. Thus, the demand for a low-molecular-weight organic compound for labeling mitochondria, which has a small size and causes no gene mutation, is increasing.

PATENT DOCUMENT

Korean Patent Application Publication No. 10-2009-0119283 (Laid-open date: Nov. 19, 2009), entitled "Development of protein over-expression system using green fluorescence protein"

SUMMARY OF THE INVENTION

Accordingly, the present invention has been made keeping in mind the above problems encountered in the related art, and the present invention is intended to provide a compound for specifically labeling mitochondria and a method of producing the same.

Therefore, the present invention is realized by the following embodiments.

An embodiment of the present invention provides a compound represented by Chemical Formula 1 or Chemical Formula 2 below:

[Chemical Formula 1]

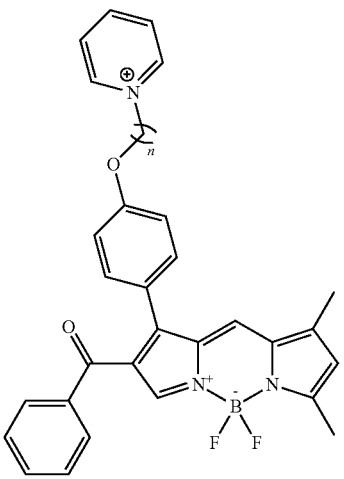

[Chemical Formula 2]

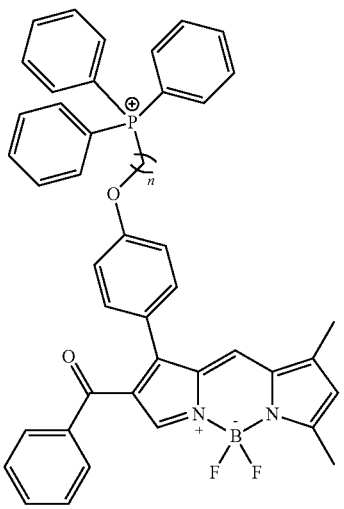

in Chemical Formulas 1 and 2, n is 4 or 10.

In the embodiment of the present invention, the compound of the invention may be used to label mitochondria.

Another embodiment of the present invention provides a method of producing a compound for labeling mitochondria, comprising: reacting a compound represented by Chemical Formula 3 below with acetonitrile, potassium iodide and pyridine, thus forming a compound represented by Chemical Formula 1 below:

[Chemical Formula 1]

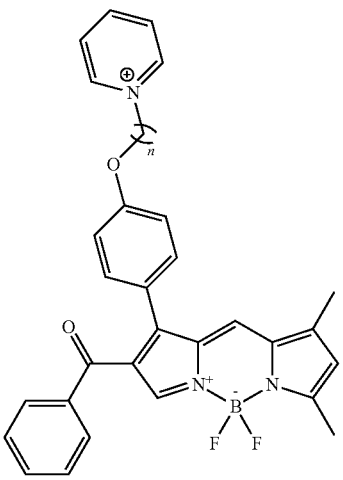

-continued

[Chemical Formula 3]

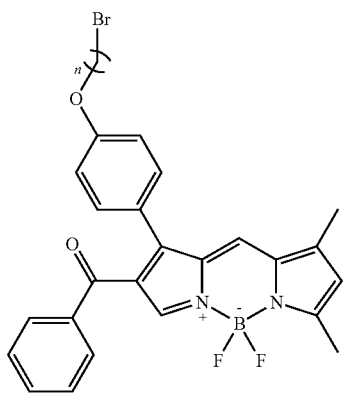

in Chemical Formulas 1 and 3, n is 4 or 10.

Still another embodiment of the present invention provides a method of producing a compound for labeling mitochondria, comprising: reacting a compound represented by Chemical Formula 3 below with acetonitrile, potassium iodide and triphenylphosphine, thus forming a compound represented by Chemical Formula 2 below:

[Chemical Formula 2]

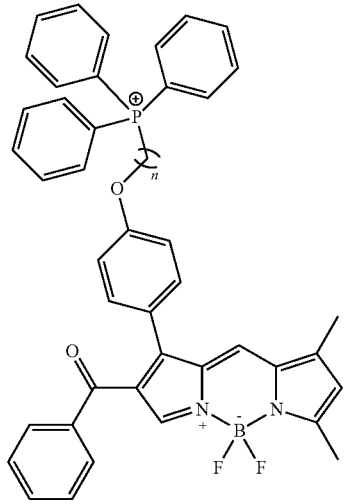

[Chemical Formula 3]

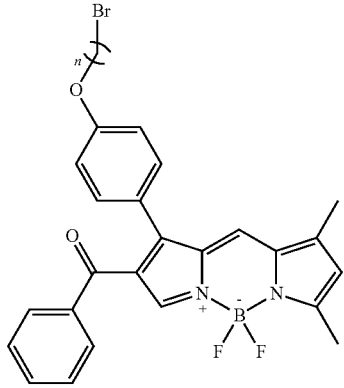

in Chemical Formulas 2 and 3, n is 4 or 10.

In the method of producing the compound for labeling mitochondria according to the embodiment of the present invention, the compound represented by Chemical Formula 3 may be formed by reacting a compound represented by Chemical Formula 4 below with methylene chloride, 2,4-dimethylpyrrole, phosphoryl chloride, boron trifluoride etherate, and diisopropylethylamine:

[Chemical Formula 4]

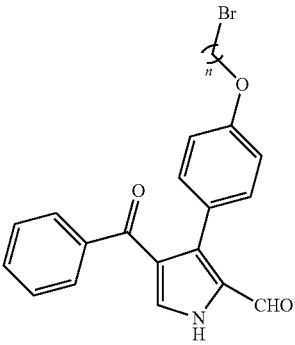

in Chemical Formula 4, n is 4 or 10.

In the method of producing the compound for labeling mitochondria according to the embodiment of the present invention, the compound represented by Chemical Formula 4 may be formed by reacting a compound represented by Chemical Formula below with dimethylformamide, phosphoryl chloride, dichloroethane, and sodium acetate:

[Chemical Formula 5]

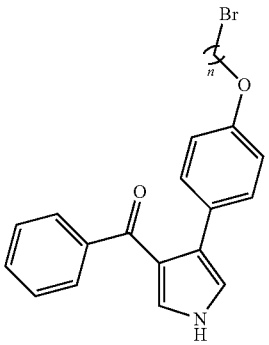

in Chemical Formula 5, n is 4 or 10.

In the method of producing the compound for labeling mitochondria according to the embodiment of the present invention, the compound represented by Chemical Formula 5 may be formed by dissolving acetophenone and (bromoalkoxy)benzaldehyde in ethanol, performing stirring, further adding lithium hydroxide monohydrate and tosylmethyl isocyanide, and performing stirring until a precipitate is generated.

Yet another embodiment of the present invention provides a method of labeling mitochondria using the compound represented by Chemical Formula 1 or 2.

The present invention can exhibit the following effects via the above embodiments.

Also, the present invention is effective at labeling mitochondria using a newly synthesized organic compound.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 show fluorescence microscopic images of labeling of mitochondria using the compound according to an embodiment of the present invention.

DESCRIPTION OF SPECIFIC EMBODIMENTS

Hereinafter, a detailed description will be given of a compound for labeling mitochondria and a method of producing the same according to the present invention, with reference to the appended drawings. Unless otherwise defined, all terms used herein have the same meaning as commonly understood by one of ordinary skill in the art to which the present invention belongs. If the meaning of the term used herein conflicts with the general meaning thereof, it accords to the definition used herein. In the following description of the present invention, detailed descriptions of known constructions and functions incorporated herein will be omitted when they may make the gist of the present invention unclear. As used herein, when any part "comprises" or "includes" any element, it means that other elements are not precluded but may be further included, unless otherwise mentioned.

An embodiment of the present invention addresses a compound for labeling mitochondria, the compound being represented by Chemical Formula 1 or Chemical Formula 2 below, in which n is 4 or 10.

[Chemical Formula 1]

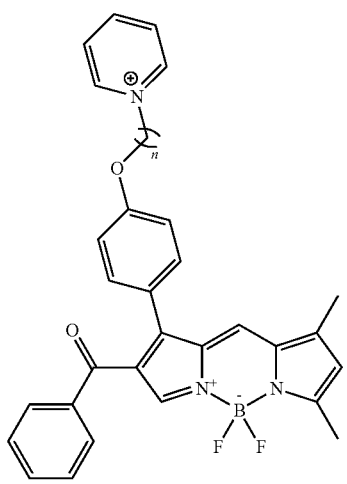

[Chemical Formula 2]

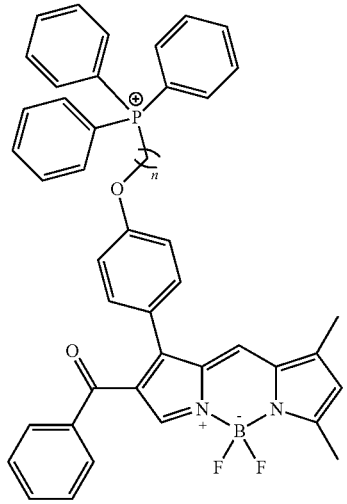

Another embodiment of the present invention addresses a method of producing a compound represented by Chemical Formula 1 or Chemical Formula 2, comprising preparing a pyrrole compound, formylating pyrrole, synthesizing a BODIPY compound, and synthesizing a BODIPY derivative.

Specifically, in the preparing the pyrrole compound, as shown in Scheme 1 below, acetophenone and (bromoalkoxy)benzaldehyde are dissolved in ethanol, stirred, reacted with lithium hydroxide monohydrate, added with lithium hydroxide monohydrate and tosylmethyl isocyanide, and stirred until a precipitate is generated, thus producing a compound represented by Chemical Formula 5 below, after which the precipitate is washed with a mixed solution of ice water and ethanol and dried.

[Scheme 1]

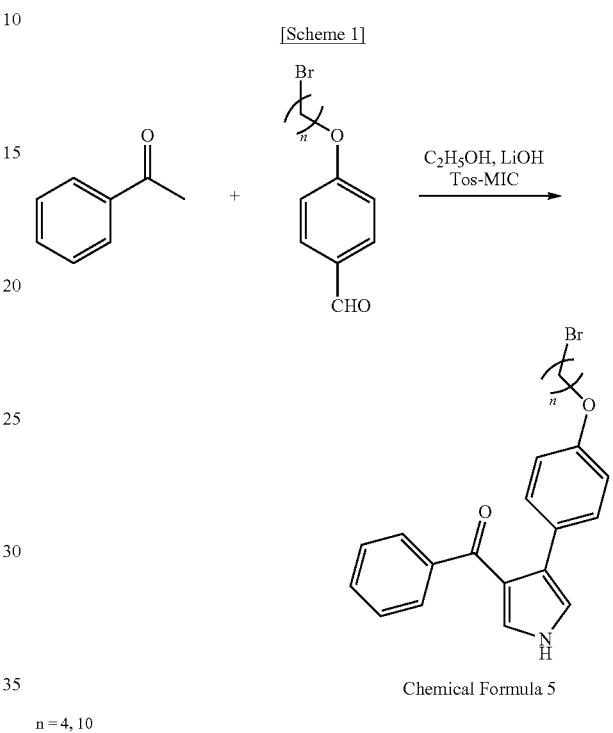

Chemical Formula 5 n = 4, 10

In the formylating the pyrrole, as shown in Scheme 2 below, the compound represented by Chemical Formula 5 is reacted with dimethylformamide (DMF) and phosphoryl chloride ($POCl_3$), further reacted with dichloroethane, and additionally reacted with sodium acetate, thus producing a compound represented by Chemical Formula 4 below, which is then extracted into the organic layer using a sodium chloride solution (brine) and subjected to column chromatography.

[Scheme 2]

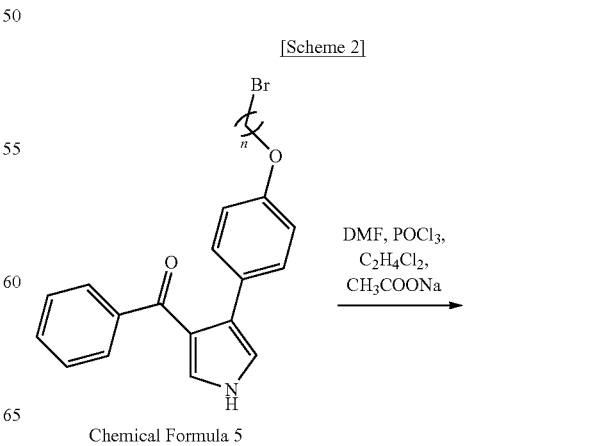

Chemical Formula 5

In the synthesizing the BODIPY derivative, as shown in Scheme 4 below, the compound represented by Chemical Formula 3 is reacted with acetonitrile, and further reacted with potassium iodide (KI) and pyridine. After the completion of the reaction, the solvent is removed from the reaction solution, thus producing a compound represented by Chemical Formula 1 below, which is then separated through column chromatography. When triphenylphosphine is added in lieu of pyridine in the synthesizing the BODIPY derivative, the compound of Chemical Formula 2 may be obtained. Here, pyridine and triphenylphosphine act as a functional group targeting mitochondria.

[Scheme 4]

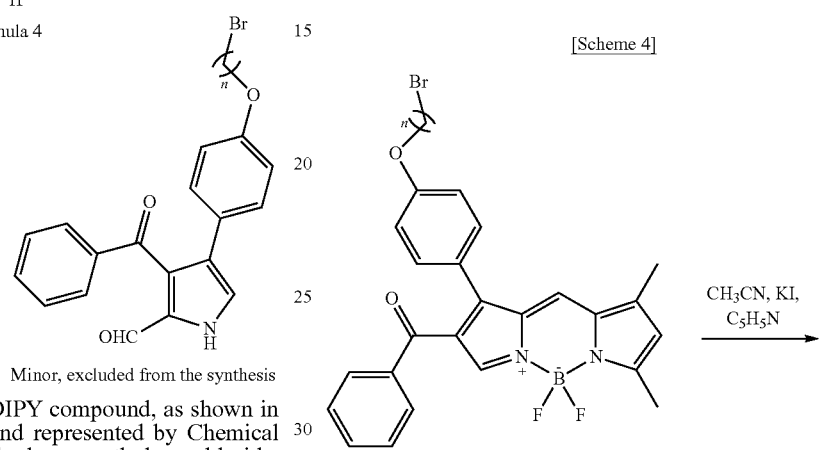

In the synthesizing the BODIPY compound, as shown in Scheme 3 below, the compound represented by Chemical Formula 4 is dissolved in anhydrous methylene chloride, reacted with 2,4-dimethylpyrrole and phosphoryl chloride, and further reacted with boron trifluoride etherate (BF$_3$OEt$_2$) and diisopropylethylamine (DIPEA), thus producing a compound represented by Chemical Formula 3 below, which is then subjected to column chromatography.

[Scheme 3]

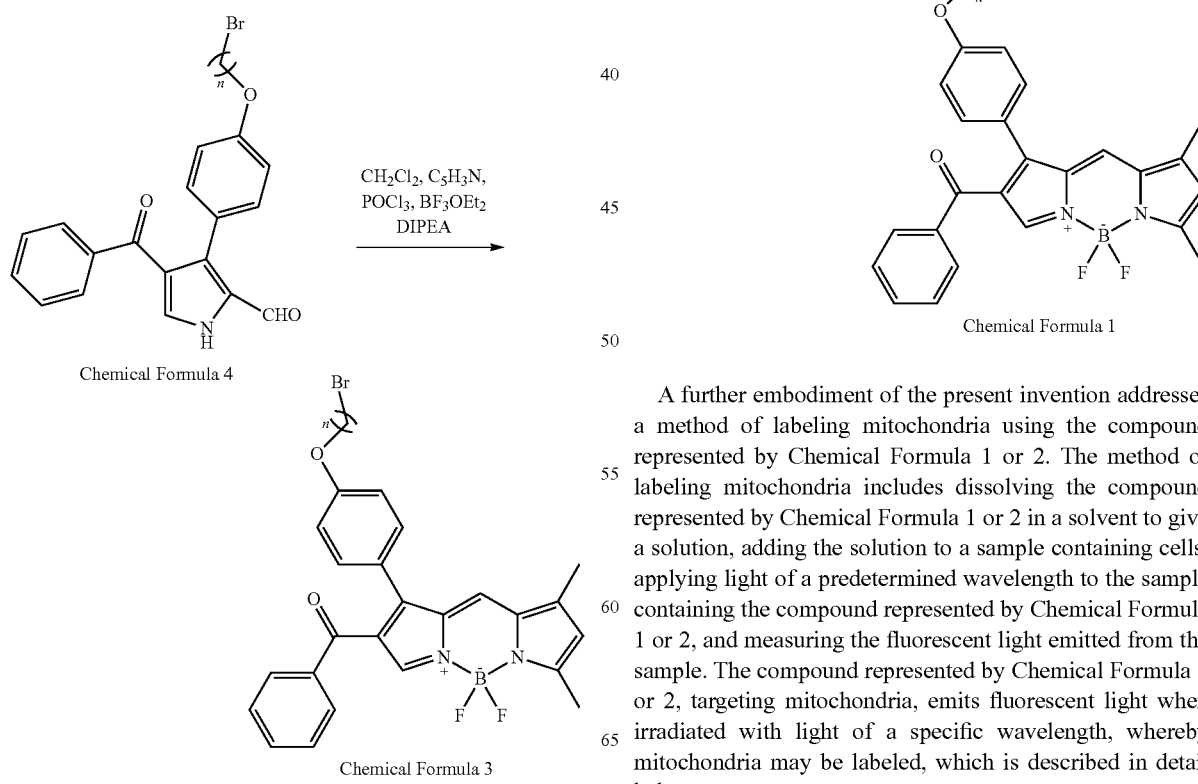

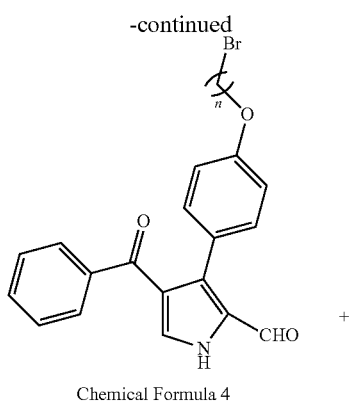

A further embodiment of the present invention addresses a method of labeling mitochondria using the compound represented by Chemical Formula 1 or 2. The method of labeling mitochondria includes dissolving the compound represented by Chemical Formula 1 or 2 in a solvent to give a solution, adding the solution to a sample containing cells, applying light of a predetermined wavelength to the sample containing the compound represented by Chemical Formula 1 or 2, and measuring the fluorescent light emitted from the sample. The compound represented by Chemical Formula 1 or 2, targeting mitochondria, emits fluorescent light when irradiated with light of a specific wavelength, whereby mitochondria may be labeled, which is described in detail below.

A better understanding of the present invention may be obtained via the following examples, which are set forth to illustrate, but are not to be construed as limiting the scope of the present invention.

<Example 1> Preparation of Compound for Labeling Mitochondria (1) Synthesis of Compound of Chemical Formula 1-1

Acetophenone (1 mmol) and (bromoalkoxy)benzaldehyde (1 mmol, n is 10) were dissolved in ethanol (3 mL), stirred, added with lithium hydroxide monohydrate (0.1 mmol), and reacted at room temperature for one day. Thereafter, lithium hydroxide monohydrate (1.1 mmol) and tosylmethyl isocyanide (1.2 mmol) were added, and the resulting mixture was stirred until a precipitate was generated, after which the precipitate was washed with a mixed solution of ice water and ethanol and dried, thus obtaining a compound represented by Chemical Formula 1-1 below.

[Chemical Formula 1-1]

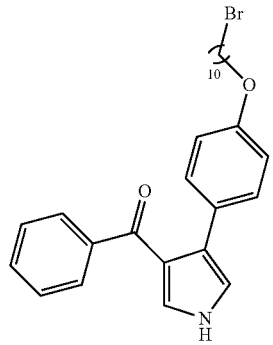

(2) Synthesis of Compound of Chemical Formula 1-2

The compound represented by Chemical Formula 1-1 (1 mmol) was added with dimethylformamide (1.2 mmol) and phosphoryl chloride (1.2 mmol) (at 0° C.), reacted at room temperature for 15 min, added with dichloroethane (15 mL) at 0° C., reacted for 30 min, further added with sodium acetate (5.5 mmol) at room temperature, and reacted for 30 min, after which the corresponding compound was extracted into the organic layer using a sodium chloride solution (brine), followed by column chromatography, thus obtaining a compound represented by Chemical Formula 1-2 below.

[Chemical Formula 1-2]

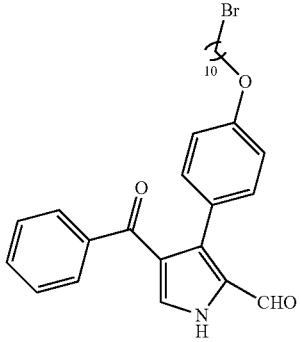

(3) Synthesis of Compound of Chemical Formula 1-3

The compound represented by Chemical Formula 1-2 (1.0 mmol) was dissolved in anhydrous methylene chloride (4 mL), cooled to −5° C., added with 2,4-dimethylpyrrole (1 mmol) and phosphoryl chloride (1 mmol), reacted for 3 hr, added with boron trifluoride etherate (3 mmol) and diisopropylethylamine (3 mmol) and reacted for 3 hr, thus producing a compound, which was then separated through column chromatography, thereby obtaining a compound represented by Chemical Formula 1-3 below.

[Chemical Formula 1-3]

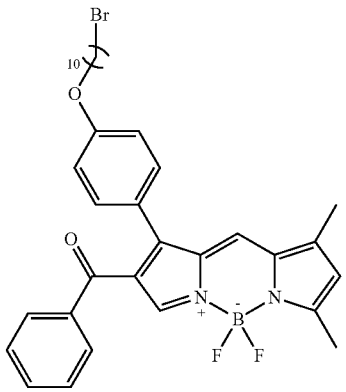

(4) Synthesis of Compound of Chemical Formula 1-4

The compound represented by Chemical Formula 1-3 (1.0 mmol) was reacted with acetonitrile (10 mL), added with potassium iodide (2 mmol) and pyridine (12 mmol), and reacted for 24 hr. After the completion of the reaction, the solvent was removed from the reaction solution, thus preparing a compound, which was then separated through column chromatography, thereby yielding a compound represented by Chemical Formula 1-4 below. The final compound represented by Chemical Formula 1-4 was confirmed through proton NMR spectroscopy and carbon NMR spectroscopy, as shown in Table 1 below.

[Chemical Formula 1-4]

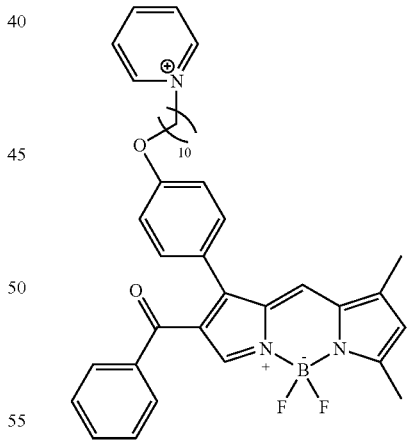

TABLE 1

| | |
|---|---|
| $^1$H NMR spectroscopy | (CDCl$_3$, 400 MHz): 9.35(d, $^3J_{(H,H)}$ = 5.2 Hz, 2H), 8.52(t, $^3J_{(H,H)}$ = 7.6 Hz, 1H), 8.11(t, $^3J_{(H,H)}$ = 8 Hz, 2H), 7.89(S, 1H), 7.78(d, $^3J_{(H,H)}$ = 5.2 Hz, 2H), 7.53(t, $^3J_{(H,H)}$ = 7.6 Hz, 1H), 7.42(t, $^3J_{(H,H)}$ = 8 Hz, 2H), 7.35(d, $^3J_{(H,H)}$ = 6.4 Hz, 2H), 7.20(s, 1H), 6.93(d, $^3J_{(H,H)}$ = 5.2 Hz, 2H), 6.30(S, 1H), 4.91(t, $^3J_{(H,H)}$ = 7.6 Hz, 2H), 3.98(t, $^3J_{(H,H)}$ = 6.4 Hz, 2H), 2.65(s, 3H), 2.29(s, 3H), 2.06-2.01(m, 2H), 1.80-1.75 (m, 2H), 1.47-1.34(m, 12H) |

TABLE 1-continued

| | |
|---|---|
| $^{13}$C NMR spectroscopy | 190.68, 159.52, 145.26, 144.81, 141.62, 139.12, 132.22, 131.59, 129.26, 128.49, 124.53, 124.54, 114.49, 68.04, 62.31, 31.81, 29.71, 29.21, 29.12, 29.07, 28.84, 25.89, 11.76. (Yield 18%); |
| ES-MS | [M + H]$^+$ = 635.2178 (cal.), 635.2717 (exp.). |

<Example 2> Evaluation of Labeling of Mitochondria Using the Compound Produced in Example 1

(1) When HeLa cells were grown to about 70~80% on a 96-well plate, the compound represented by Chemical Formula 1-4 was added at a concentration of 1 μM into each well, and the plate was placed in a 5% $CO_2$ incubator at 37° C. for 1 hr, after which the medium was removed. The resulting product was washed once with a PBS buffer, refilled with 100 μL of a medium, and observed using a fluorescence microscope (DMi8 available from Leica, a light source at 480 nm, a filter at 527 nm). The obtained image is shown in FIG. 1B.

(2) As a control, Hoechst 34580 for tracking nuclei was added in lieu of the compound of Chemical Formula 1-4, and the obtained florescence microscopic image (a light source at 350 nm, a filter at 460 nm) is shown in FIG. 1A. Also, MitoTracker Orange CMTMRos for tracking mitochondria was added in lieu of the compound of Chemical Formula 1-4, and the obtained florescence microscopic image (a light source at 546 nm, a filter at 585 nm) is shown in FIG. 1C. FIG. 1D shows corresponding bright field results.

(3) With reference to FIGS. 1A to 1D, the results obtained using the compound of Chemical Formula 1-4 (FIG. 1B) matched the results obtained using the MitoTracker Orange CMTMRos for tracking mitochondria (FIG. 1C). Therefore, the compound of the present invention can be concluded to be useful in labeling (imaging) mitochondria.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A compound represented by Chemical Formula 1 or Chemical Formula 2 below:

[Chemical Formula 1]

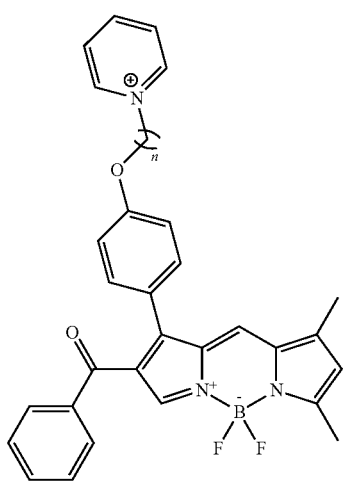

[Chemical Formula 2]

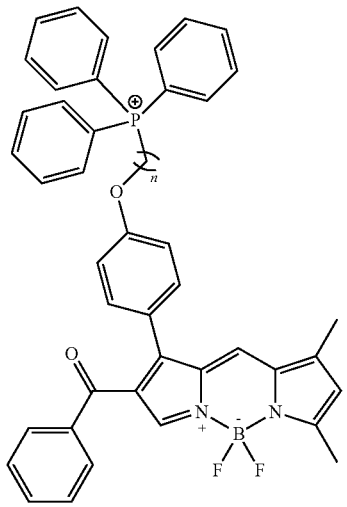

in Chemical Formulas 1 and 2, n is 4 or 10.

2. A method of producing a compound for labeling mitochondria, comprising:
reacting a compound represented by Chemical Formula 3 below with acetonitrile, potassium iodide and pyridine, thus forming a compound represented by Chemical Formula 1 below:

[Chemical Formula 1]

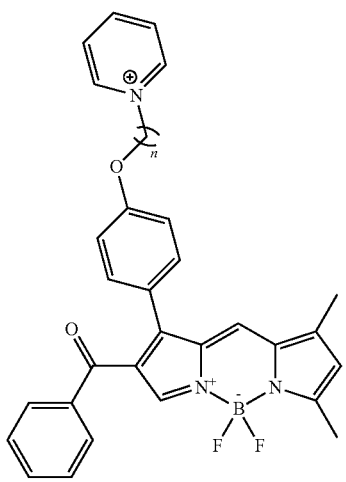

[Chemical Formula 3]

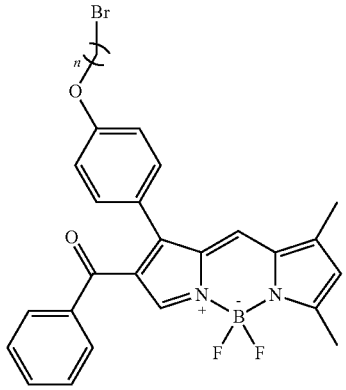

in Chemical Formulas 1 and 3, n is 4 or 10.

3. A method of producing a compound for labeling mitochondria, comprising:

reacting a compound represented by Chemical Formula 3 below with acetonitrile, potassium iodide and triphenylphosphine, thus forming a compound represented by Chemical Formula 2 below:

[Chemical Formula 2]

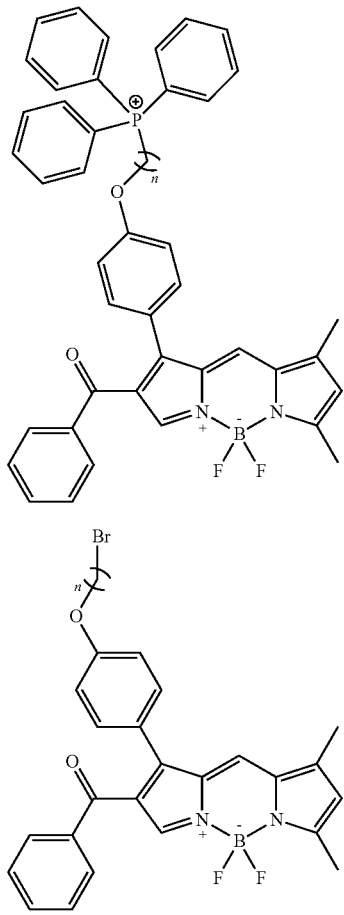

[Chemical Formula 3]

in Chemical Formulas 2 and 3, n is 4 or 10.

4. The method of claim 2, wherein the compound represented by Chemical Formula 3 is formed by reacting a compound represented by Chemical Formula 4 below with methylene chloride, 2,4-dimethylpyrrole, phosphoryl chloride, boron trifluoride etherate, and diisopropylethylamine:

[Chemical Formula 4]

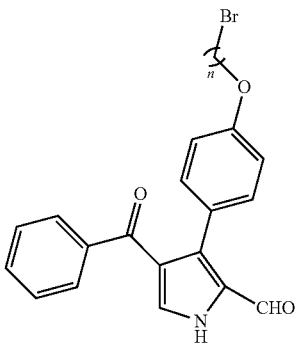

in Chemical Formula 4, n is 4 or 10.

5. The method of claim 4, wherein the compound represented by Chemical Formula 4 is formed by reacting a compound represented by Chemical Formula 5 below with dimethylformamide, phosphoryl chloride, dichloroethane, and sodium acetate:

[Chemical Formula 5]

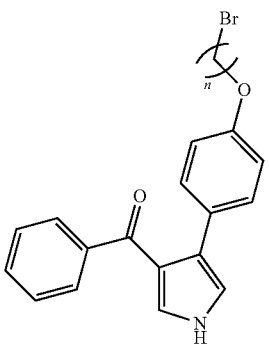

in Chemical Formula 5, n is 4 or 10.

6. The method of claim 5, wherein the compound represented by Chemical Formula 5 is formed by dissolving acetophenone and (bromoalkoxy)benzaldehyde in ethanol, performing stirring, further adding lithium hydroxide monohydrate and tosylmethyl isocyanide, and performing stirring until a precipitate is generated.

7. A method of labeling mitochondria comprising dissolving the compound represented by Chemical Formula 1 or 2 of claim 1 in a solvent to give a solution and adding the solution to a sample containing cells.

* * * * *